(12) United States Patent
Williams

(10) Patent No.: US 11,801,013 B2
(45) Date of Patent: Oct. 31, 2023

(54) METHOD AND SYSTEM OF DEPLOYING PORTABLE BREATH ALCOHOL MONITORING DEVICE

(71) Applicant: Consumer Safety Technology LLC, Des Moines, IA (US)

(72) Inventor: Kimberly Williams, Des Moines, IA (US)

(73) Assignee: Consumer Safety Technology, LLC, Des Moines, IA (US)

( * ) Notice: Subject to any disclaimer, the term of this patent is extended or adjusted under 35 U.S.C. 154(b) by 150 days.

(21) Appl. No.: 17/096,339

(22) Filed: Nov. 12, 2020

(65) Prior Publication Data

US 2022/0142585 A1    May 12, 2022

(51) Int. Cl.
*A61B 5/00* (2006.01)
*A61B 5/08* (2006.01)
*G01N 33/497* (2006.01)
*A61B 5/11* (2006.01)

(52) U.S. Cl.
CPC ............ *A61B 5/7221* (2013.01); *A61B 5/082* (2013.01); *A61B 5/4845* (2013.01); *A61B 5/6893* (2013.01); *G01N 33/4972* (2013.01); *A61B 5/0077* (2013.01); *A61B 5/1112* (2013.01); *A61B 2562/0219* (2013.01)

(58) Field of Classification Search
CPC ..... A61B 5/7221; A61B 5/082; A61B 5/4845; A61B 5/6893; G01N 33/4972
USPC ........................................................ 340/500
See application file for complete search history.

(56) References Cited

U.S. PATENT DOCUMENTS

| | | | |
|---|---|---|---|
| 5,426,415 A | 6/1995 | Prachar et al. |
| 6,167,746 B1 | 1/2001 | Gammenthaler |
| 6,748,792 B1 | 6/2004 | Freund et al. |
| 6,853,956 B2 | 2/2005 | Ballard et al. |
| 6,956,484 B2 | 10/2005 | Crespo et al. |
| 7,135,788 B2 | 11/2006 | Metlitzky et al. |
| 8,078,334 B2 | 12/2011 | Goodrich |

(Continued)

FOREIGN PATENT DOCUMENTS

| | | |
|---|---|---|
| CA | 2366341 | 5/2010 |
| WO | 2022157538 | 7/2022 |

OTHER PUBLICATIONS

"Ignition Interlocks—What You Need to Know: A Toolkit for Policymakers, Highway Safety Professionals, and Advocates (2nd Edition)," National Technical Information Service www.ntis.gov, Feb. 2014, pp. 1-60.

(Continued)

*Primary Examiner* — Kerri L McNally
(74) *Attorney, Agent, or Firm* — Pauly, DeVries Smith & Deffner LLC

(57) ABSTRACT

A system and method of deploying a portable breath alcohol monitoring device. The method comprises inferring a rate of motion associated with the portable breath alcohol monitoring device; initiating, at a display screen of the portable breath alcohol monitoring device when the rate of motion is above a predetermined threshold, a request for a breath sample; determining, responsive to the request for the breath sample at the portable breath alcohol monitoring device, a violation; and reporting the violation to a remote server communicatively coupled to the portable breath alcohol monitoring device.

19 Claims, 3 Drawing Sheets

(56) References Cited

U.S. PATENT DOCUMENTS

| | | | |
|---|---|---|---|
| 8,359,901 B2 | 1/2013 | Freund et al. | |
| 8,493,219 B2 | 7/2013 | Buck et al. | |
| 8,640,813 B2 | 2/2014 | Doinoff et al. | |
| 8,957,771 B2 * | 2/2015 | Arringdale | B60K 28/063 340/576 |
| 9,239,323 B2 | 1/2016 | Keays | |
| 9,442,103 B1 | 9/2016 | Goad | |
| 9,481,245 B2 | 11/2016 | Nelson et al. | |
| 9,668,095 B1 | 5/2017 | Newell et al. | |
| 9,878,660 B1 * | 1/2018 | Hodge | G08G 1/0175 |
| 9,908,488 B2 | 3/2018 | Shafer | |
| 10,040,458 B2 | 8/2018 | Morley et al. | |
| 10,074,261 B2 | 9/2018 | Buck et al. | |
| 10,085,683 B1 | 10/2018 | Sham | |
| 10,467,883 B2 | 11/2019 | Buck et al. | |
| 10,621,852 B2 | 4/2020 | Buck et al. | |
| 10,650,663 B2 | 5/2020 | Buck et al. | |
| 10,692,345 B1 | 6/2020 | Newell | |
| 10,902,613 B2 | 1/2021 | Newell | |
| 10,919,389 B2 | 2/2021 | DeVries et al. | |
| 11,037,434 B2 | 6/2021 | Buck et al. | |
| 11,047,840 B2 | 6/2021 | DeVries et al. | |
| 11,164,444 B2 | 11/2021 | Buck et al. | |
| 11,250,688 B2 | 2/2022 | Buck et al. | |
| 11,270,564 B2 | 3/2022 | Newell | |
| 11,494,917 B2 | 11/2022 | Newell | |
| 2003/0117287 A1 * | 6/2003 | Crespo | G08B 13/19647 340/576 |
| 2005/0136947 A1 * | 6/2005 | Llombart-Juan | G01C 21/20 455/414.1 |
| 2014/0335905 A1 | 11/2014 | Bhoot | |
| 2015/0197151 A1 | 7/2015 | Ballard | |
| 2015/0244452 A1 | 8/2015 | Wojciech et al. | |
| 2015/0249906 A1 | 9/2015 | Thomas et al. | |
| 2016/0081587 A1 * | 3/2016 | Ghazarian | G06V 20/59 600/301 |
| 2016/0086021 A1 | 3/2016 | Grohman et al. | |
| 2017/0282713 A1 | 10/2017 | DeVries et al. | |
| 2017/0313189 A1 | 11/2017 | Walter et al. | |
| 2018/0011068 A1 | 1/2018 | Lyon | |
| 2018/0209955 A1 | 7/2018 | Moeller | |
| 2019/0246958 A1 | 8/2019 | Moeller et al. | |
| 2019/0376949 A1 | 12/2019 | Lyon | |
| 2020/0361314 A1 | 11/2020 | Ringgenberg et al. | |
| 2020/0367801 A1 | 11/2020 | Hanson et al. | |
| 2021/0148892 A1 | 5/2021 | Ruland et al. | |
| 2021/0156834 A1 | 5/2021 | DeVries et al. | |
| 2022/0142586 A1 | 5/2022 | Williams | |
| 2022/0146616 A1 | 5/2022 | Newell | |
| 2022/0315008 A1 | 10/2022 | Smith et al. | |
| 2023/0028690 A1 | 1/2023 | Woods et al. | |

OTHER PUBLICATIONS

"Intoxalock eLERT Brochure," Available at least as early as Oct. 20, 2016, pp. 1-3.

"Intoxalock eLERT System Feature Description," available at least as early as Nov. 11, 2019, 1 page.

"Intoxalock eLERT User Manual," www.intoxalock.com, last revised Jan. 25, 2016, pp. 1-10.

"Intoxalock Log Reporter," www.intoxalock.com, available at least as early as Oct. 2, 2017, pp. 1-6.

"Non-Final Office Action," for U.S. Appl. No. 17/158,851 dated Nov. 14, 2022 (21 pages).

"Final Office Action," for U.S. Appl. No. 17/158,851 dated May 1, 2023 (22 pages).

"Response to Non Final Office Action," for U.S. Appl. No. 17/158,851, filed Apr. 14, 2023 (12 pages).

"Notice of Allowance," for U.S. Appl. No. 17/158,851 dated Jun. 12, 2023 (10 pages).

* cited by examiner

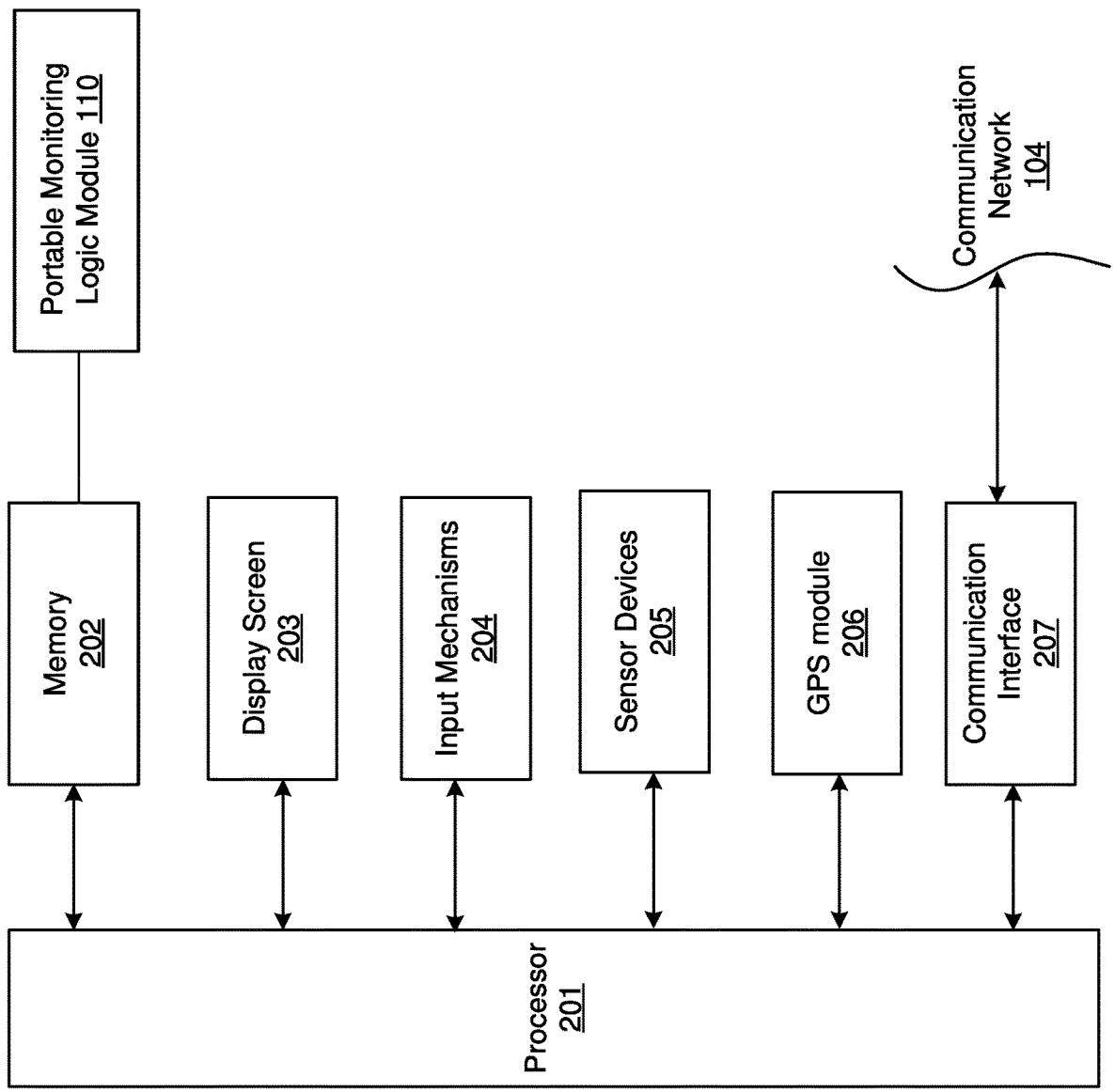

300

```
┌─────────────────────────────────────────────────────────────┐
│  Inferring a rate of motion associated with the portable    │
│  breath alcohol monitoring device                           │
│                                                         310 │
└─────────────────────────────────────────────────────────────┘
                              │
                              ▼
┌─────────────────────────────────────────────────────────────┐
│  Initiating, at a display screen of the portable breath     │
│  alcohol monitoring device when the rate of motion is above │
│  a predetermined threshold, a request for a breath sample   │
│                                                         320 │
└─────────────────────────────────────────────────────────────┘
                              │
                              ▼
┌─────────────────────────────────────────────────────────────┐
│  Determining, responsive to the request for the breath      │
│  sample, a violation                                        │
│                                                         330 │
└─────────────────────────────────────────────────────────────┘
                              │
                              ▼
┌─────────────────────────────────────────────────────────────┐
│  Reporting the violation to a remote server communicatively │
│  coupled to the portable breath alcohol monitoring device   │
│                                                         340 │
└─────────────────────────────────────────────────────────────┘
```

FIG. 3

METHOD AND SYSTEM OF DEPLOYING PORTABLE BREATH ALCOHOL MONITORING DEVICE

TECHNICAL FIELD

The disclosure herein relates to methods and systems of deploying portable breath alcohol monitoring and testing devices.

BACKGROUND

Vehicles can incorporate a breath alcohol ignition interlock device (IID) to prevent a driver from operating a vehicle while intoxicated with alcohol. Such devices are designed to prevent a driver from starting a motor vehicle when the driver's breath alcohol content (BrAC) is at or above a mandated alcohol concentration threshold. Various jurisdictions have adopted a law providing for use of such IID devices as a sanction for drivers convicted of driving while intoxicated, or as a condition of restoring driving privileges during some probationary period after such offenses. A typical IID device meets guidelines established by the National Highway Traffic Safety Administration (NHTSA) in published model specifications for IIDs, which specify various tests that such a device must pass to make it an effective and reliable deterrent to intoxicated driving.

BRIEF DESCRIPTION OF THE DRAWINGS

FIG. 2 illustrates an example architecture of a portable breath alcohol monitoring device deployed within a computing and communication system.

FIG. 3 illustrates, in an example embodiment, a method of deploying a portable breath alcohol monitoring device within a computing and communication system.

DETAILED DESCRIPTION

Figure 1:
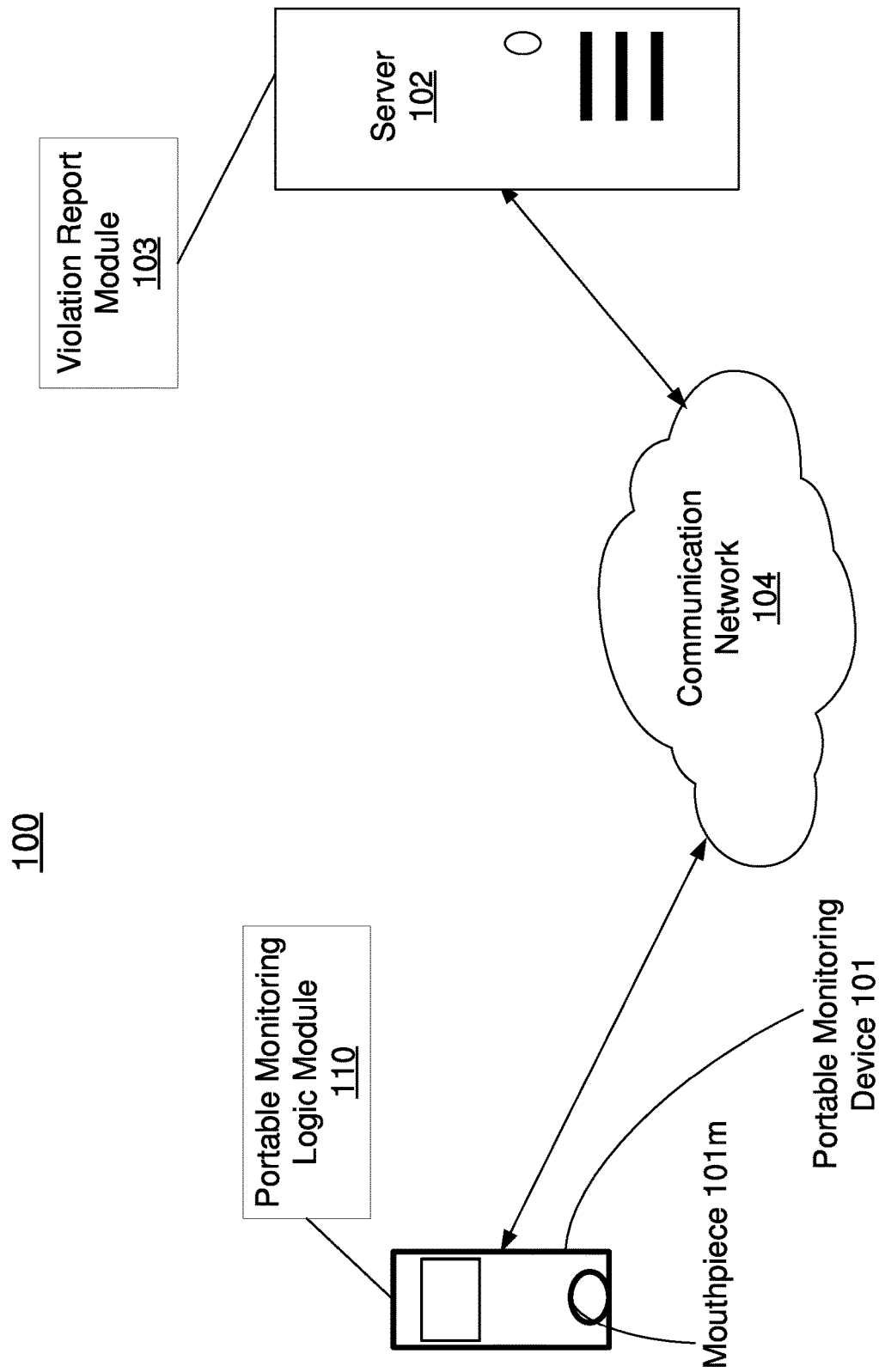
FIG. 1 illustrates a portable breath alcohol monitoring device deployed within a computing and communication system in accordance with embodiments herein.

Embodiments herein recognize that IID devices are not portable, and yet further, can be hacked or tampered with. For example, an impaired driver can have a sober person blow into the breathalyzer, in a circumvention attempt, to activate vehicle ignition for operation.

Among other benefits and technical effects, embodiments herein provide a method and system of deploying supervisory monitoring of alcohol impairment that is discreet, portable, tamper-resistant, and effective. Embodiments herein also provide for automatically transmitting a user's breath alcohol testing data, and for notifying or alerting a monitoring remote server station of possible violations in a real-time basis in violation of a pre-existing probation condition. Yet further, embodiments herein provide a method and system for immediate, real-time confirmation independent of any particular vehicle control module, upon detecting that, in violation of an existing probation order that prohibits operation of a vehicle, the user may in fact be driving a vehicle.

Embodiments herein also provide an alternate option for drivers arrested for impaired driving, but who opt not to install a vehicle IID, and instead "choose not to drive." Such impaired driving offenders, as a condition associated with probation, may use a portable breath alcohol tester should they choose not to install a vehicle IID. Based on detecting traversal speeds faster than typical pedestrian rates of motion of a carried personal breath alcohol monitoring device, embodiments herein can trigger a request for breath alcohol content (BrAC) test, in conjunction with image-based user authentication or user driving status confirmation in some variations, of a user driving while carrying the portable breath alcohol monitoring device. In some embodiments, a user of the portable breath tester device is presented with the request for breath sample contemporaneously with capturing successive digital images of the user within the vehicle until the breath test is completed. In this manner, digital images of the user or vehicle operator can be captured, timestamped for the time the breath test was requested and also periodically until test is complete. Such sequence of breath tests and associated image captures of the user or operator of the vehicle can preempt, discourage or minimize attempts at circumvention, for instance, a driver switching out of the drivers' seat within a vehicle. In some variations, the digital image capture can be provided by one or more wide angle camera lenses located within the vehicle, in addition to, or in lieu of, any image capture capability incorporated into the portable breath tester, capturing timestamped image data for communication to the portable breath tester by Bluetooth or similar wireless communication means.

Embodiments herein further provide for classifying as a violation a user's refusal of, or non-compliance with, a request for a breath sample. In this manner, a user is pre-empted from circumventing an applicable prohibition against their operating a vehicle.

Provided is a method of deploying a portable breath alcohol monitoring device. The method comprises inferring a rate of motion associated with the portable breath alcohol monitoring device; initiating, at a display screen of the portable breath alcohol monitoring device when the rate of motion is above a predetermined threshold, a request for a breath sample; determining, responsive to the request for the breath sample, a violation; and reporting the violation to a remote server communicatively coupled to the portable breath alcohol monitoring device.

Further provided is a server computing device including a computer readable, non-transitory memory including executable instructions, the instructions when executed in a processor causing operations comprising inferring a rate of motion associated with a portable breath alcohol monitoring device communicatively coupled with the server computing device; initiating, at a display screen of the portable breath alcohol monitoring device when the rate of motion is above a predetermined threshold, a request for a breath sample; and determining, responsive to the request for the breath sample at the portable breath alcohol monitoring device, a violation.

Also provided is a portable breath alcohol monitoring device comprising a processor, and a memory storing a set of instructions. The instructions when executed in the processor cause operations comprising inferring a rate of motion associated with the portable breath alcohol monitoring device; initiating, at a display screen of the portable breath alcohol monitoring device when the rate of motion is above a predetermined threshold, a request for a breath sample; determining, responsive to the request for the breath sample, a violation; and reporting the violation to a remote server communicatively coupled to the portable breath alcohol monitoring device.

Embodiments described herein can be implemented using programmatic modules, through the use of instructions that are executable by one or more processors. A programmatic module can include a program, a sub-routine, a portion of a program, or a software component or a hardware component capable of performing one or more stated tasks or functions. As used herein, a programmatic module can exist on a hardware component independently of other modules or components, or can be a shared element of other modules, programs or machines.

Some embodiments of portable breath alcohol monitoring device described herein can generally incorporate computing and communication resources, such as processor and memory resources. For example, one or more embodiments of portable breath alcohol monitoring device described herein may be implemented, in whole or in part, on wearable monitoring devices, and also in conjunction with tablet devices and smartphone devices. Memory, processing, and network resources may all be used in connection with the establishment, use, or performance of any embodiment described herein, including with the performance of any method or with the implementation of any system.

One or more embodiments described herein provide that methods, techniques, and actions performed by a portable breath alcohol monitoring device are performed programmatically, or as a computer-implemented method. Programmatically, as used herein, means through the use of code or computer-executable instructions. These instructions can be stored in one or more memory resources of the portable breath alcohol monitoring device.

Device and System

FIG. 1 illustrates a portable breath alcohol monitoring device 101 deployed within portable breath monitoring system 100 in accordance with embodiments herein. Portable breath alcohol monitoring device 101 includes a processor and a memory. The memory stores executable instructions, constituting portable breath alcohol monitoring logic module 110 for deploying portable breath alcohol monitoring device 101 into reporting a user violation related to a prohibition on driving a vehicle. In variations, some portions, or all, of the executable instructions constituting portable breath alcohol monitoring logic module 110 may be hosted at violation report server 102 in communication with portable breath alcohol monitoring device 101 via communication network 104. If a user, or vehicle operator while in possession of portable breath alcohol monitoring device 101 is authenticated and identified as driver of a vehicle consistent with a rate of motion that indicates operation of the vehicle, then portable breath alcohol monitoring device 101 will trigger a violation report to violation report server 102. Violation report module 103 of violation report server 102 includes logic related to storing rate of motion and breath alcohol measurements and driver identification digital image-based results communicated from portable breath alcohol device 101. In some variations, violation report module 103 of violation report server 102 enable final determinations as to whether a driving-related violation has occurred. In some embodiments herein, BrAC measurements from a user breath sample received at a mouthpiece 101m of portable breath alcohol monitoring device 101 can be correlated with blood alcohol content (BAC) levels, and a violation report can also be triggered based on either of a measured BrAC or a correlating BAC. It is contemplated that such BrAC and BAC correlations may be performed either locally at portable breath alcohol monitoring device 101 or at violation report server 102.

FIG. 2 illustrates example architecture 200 of portable breath alcohol monitoring device 101 deployed within portable breath monitoring system 100. In one embodiment, portable breath alcohol monitoring device 101 may include or be interconnected with, for example, one or more of cellular or other wireless computing and communication capable of telephony, messaging, and data computing services. Ignition interlock device may include processor 201, memory 202, display screen 203, input devices 204 such as resistive- or capacitance-based input mechanisms or software-implemented touchscreen input functionality, audible alerts capability, and sensor devices 205. Input devices 204 may also include breath sample mouthpiece 101m to receive, at portable breath alcohol monitoring device 101, a breath sample submitted by a user. Portable breath alcohol monitoring device 101 may also include capability for detecting and communicatively accessing wireless communication signals, including but not limited to any of Bluetooth, Wi-Fi, RFID, and global positioning system (GPS) signals, and incorporate communication interface 207 for communicatively coupling to communication network 104, such as by sending and receiving cellular and GPS data over data channels and voice channels. Portable breath alcohol monitoring device 101 can incorporate GPS module 206 that includes GPS receiver and transmitter circuitry for accessing and enabling GPS signals and data.

Sensor devices 205 of portable breath alcohol monitoring device 101 can include an alcohol fuel cell sensor. Breath alcohol testing and monitoring devices are operated by a user blowing into a mouthpiece 101m of the device. The breath alcohol testing and monitoring device 101 incorporates an alcohol-sensing element such as a fuel cell sensor that measures alcohol content of the driver's breath, thereby providing an objective representation or estimate of the blood alcohol concentration of the driver's bloodstream. The monitoring device reads an electrical signal generated from the fuel cell, or similar alcohol-sensing element, and determines whether an operator's breath alcohol content exceeds some pre-designated threshold amount. If the operator's breath alcohol content does not exceed the threshold, the operator is determined as not intoxicated or impaired. If the breath sample delivered from the user registers a higher breath alcohol content than the predetermined allowable threshold, portable breath alcohol monitoring device 101 generates, records and reports an impaired driving violation.

Sensor devices 205 of portable breath alcohol monitoring device 101 can also include an accelerometer sensor device used to detect an initial motion or displacement. In conjunction with detecting such initial motion or displacement of the portable breath alcohol monitoring device 101 from some initial rest position, embodiments described herein can then be activated and deployed to detect traversal speeds and possible impairment violations associated with a carried portable breath alcohol monitoring device 101.

Sensor devices 205 can further include digital imaging sensors for incorporating digital imaging capability at portable breath alcohol monitoring device 101.

Portable breath alcohol monitoring logic module 110 can be constituted of computer processor-executable code stored in memory 202 of portable breath alcohol monitoring device 101 for deploying functionality ascribed to embodiments herein. In one variation, portable breath alcohol monitoring logic module 110 may be stored in memory 202 upon subsequent accessing and downloading, via communication network 104, from violation report server 102 or other third party remote server.

In particular embodiments, portable breath alcohol monitoring logic module 110 includes instructions executable in processor 210 to infer a rate of motion associated with portable breath alcohol monitoring device 101. In some embodiments, an indication that the portable breath alcohol monitoring device 101 is in motion, for example from a prior rest position, may be received from data of an accelerometer sensor device. The accelerometer sensor device data can be from the portable breath alcohol monitoring device 101, or in other embodiments, can be acquired from a communicatively coupled smartphone, tablet or similar device.

In embodiments, a rate of motion of portable breath alcohol monitoring device 101 can be calculated based on time elapsed during travel between two successive coordinate positions traversed using data acquired from a global positioning system. Thus, inferring the rate of motion comprises calculating the rate of motion of portable breath alcohol monitoring device 101 based at least on the elapsed time duration associated with traversal between two successive coordinate positions.

In embodiments, the predetermined rate of motion threshold is stored in memory 202 of portable breath alcohol monitoring device 101. In alternate embodiments, the predetermined rate of motion threshold can be stored in a memory of violation report server 102.

Portable breath alcohol monitoring logic module 110 further includes executable instructions to initiate, at display screen 203 of portable breath alcohol monitoring device 101 when the rate of motion is above a predetermined threshold, a request for a breath sample. In embodiments, the request for breath sample is triggered when the rate of motion exceeds that attributable to pedestrian movement, such as around 10 miles per hour or under. In an example embodiment, when the rate of motion as calculated is above a pre-determined threshold, in one example embodiment designated as 25 miles per hour, then a request for a breath sample related to possible alcohol consumption or other intoxicant is generated at display screen 203 or via an audible user interface alert of portable breath alcohol monitoring device 101.

Contemporaneously with the request for providing of a breath sample, one or more camera images may be captured for identifying and authenticating a user of the portable breath alcohol monitoring device. It is also contemplated that camera images captured can be used to at least partly determine a driving status of the user; for instance, whether the user appears to be, or likely is in the driver's seat, operating a vehicle.

In some embodiments, a user of the portable breath tester device is presented with the request for breath sample contemporaneously with digital images of the user within the vehicle. In this manner, digital images of the user or vehicle operator can be captured at the time the breath test was requested and then periodically until test is complete. Such sequence of breath tests and associated image captures of the user or operator of the vehicle can preempt, discourage or minimize attempts at circumvention, for instance, a driver switching out of the drivers' seat within a vehicle. In some variations, the digital image capture can be provided by one or more wide angle camera lenses located within the vehicle, in addition to, or in lieu of, any image capture capability incorporated into the portable breath tester, capturing timestamped image data for communication to the portable breath tester by Bluetooth or similar wireless communication means.

In embodiments, authenticating comprises comparing the captured image of the user with a predesignated image stored in memory 202 of portable breath alcohol monitoring device. In alternate embodiments, the predesignated image can be stored in a memory of violation report server 102.

Portable breath alcohol monitoring logic module 110 also includes executable instructions to determine a violation. In one embodiment, a violation is determined upon not receiving a breath sample from the user within some predetermined time of the request for sample being presented at portable alcohol monitoring device 101. In one embodiment, the predetermined time for response to the request for breath sample ranges from 20 seconds to 2 minutes. Thus, a user cannot simply withhold providing a breath sample, thereby avoiding a violation and in effect circumventing the portable breath monitoring system 100 by not being compliant with a probation agreement that prohibits operating a vehicle.

In another embodiment, responsive to the request for the breath sample, determining a breath alcohol content (BrAC) of the breath sample as received at the portable breath alcohol monitoring device and determining the violation when the BrAC is above a predetermined BrAC threshold.

In yet another variation, a likely driving status of a user of the portable breath alcohol monitoring device can be ascertained based on capturing a plurality of successive images of the user within a vehicle in conjunction with the breath test request until the test is in the driver's seat of the vehicle, and driving the vehicle in violation of a prohibition against vehicle operation.

Portable breath alcohol monitoring logic module 110 also includes executable instructions to report the violation to violation report server 102 communicatively coupled to portable breath alcohol monitoring device 101.

In some embodiments, the predetermined BAC threshold is stored in memory 202 of portable breath alcohol monitoring device 101. In alternate embodiments, the predetermined BAC threshold can stored in a memory of violation report server 102, and made communicatively accessible to portable breath alcohol monitoring device 101.

In additional embodiments, the violation comprises an impaired driving violation, and reporting the violation comprises identifying the assigned user of portable breath alcohol monitoring device 101 in conjunction with at least the BrAC as determined, or a BAC correlated with the BrAC as measured. In alternate embodiments, BrAC readings acquired at portable alcohol breath monitoring device 101 can be forwarded to violation report server 102, without determination of a violation. Instead, in such alternate embodiments, a violation can be determined at violation report server 102 based on actual BrAC measurements as received from portable breath alcohol monitoring device 101.

Methodology

FIG. 3 illustrates, in example embodiment 300, a method of deploying portable breath alcohol monitoring device 101 within portable breath monitoring system 100. Examples of method steps described herein are related to deployment and use of portable breath alcohol monitoring device 101 as described herein. According to one embodiment, the techniques are performed in processor 201 executing one or more sequences of software logic instructions that constitute portable breath alcohol monitoring logic module 110 of portable breath alcohol monitoring device 101. In embodiments, portable breath alcohol monitoring logic module 110 may be remotely hosted at violation report server 102, also referred to herein as server 102, and is communicatively coupled with portable breath alcohol monitoring device 101. Such instructions may be read into memory 202 from machine-readable medium, such as memory storage devices. Executing the instructions of portable breath alcohol monitoring logic module 110 stored in memory 202 causes processor 201 to perform the process steps described herein. In alternative implementations, at least some hard-wired circuitry may be used in place of, or in combination with, the software logic instructions to implement examples described herein. Thus, the examples described herein are not limited to any particular combination of hardware circuitry and software instructions.

At step 310, inferring a rate of motion associated with portable breath alcohol monitoring device 101. In some embodiments, an initial indication that the portable breath alcohol monitoring device 101 is in motion, for example from a prior rest position, may be received from data of an included accelerometer sensor device. The accelerometer sensor device can be from the portable breath alcohol monitoring device 101, or in other embodiments, can be acquired from a communicatively coupled smartphone, tablet or similar device.

In embodiments, a rate of motion of portable breath alcohol monitoring device 101 can be calculated based on time elapsed during travel between two successive coordinate positions traversed using data acquired from a global positioning system. Thus, inferring the rate of motion comprises calculating the rate of motion of portable breath alcohol monitoring device 101 based at least on the elapsed time duration associated with traversal between two successive coordinate positions.

At step 320, initiating, at display screen 203 of portable breath alcohol monitoring device 101 when the rate of motion is above a predetermined threshold, a request for a breath sample. In embodiments, the request for breath sample is triggered when the rate of motion exceeds that attributable to pedestrian movement, such as around 10 miles per hour or under. In an example embodiment, when the rate of motion as calculated is above a pre-determined threshold, in one example embodiment designated as 25 miles per hour, then a request for a breath sample related to possible alcohol, or other intoxicant, impaired driving is generated at display screen 203 or via an audible user interface alert of portable breath alcohol monitoring device 101.

In embodiments, the predetermined rate of motion threshold is stored in memory 202 of portable breath alcohol monitoring device 101. In alternate embodiments, the predetermined rate of motion threshold can be stored in a memory of violation report server 102.

At step 330, determining, responsive to the request for the breath sample, a violation. In one embodiment, a violation is determined upon not receiving a breath sample from the user within some predetermined time of the request for sample being presented at portable alcohol monitoring device 101. Thus, a user cannot simply withhold providing a breath sample, thereby avoiding a violation and in effect circumventing the portable breath monitoring system 100 by not being compliant with a probation agreement that prohibits operating a vehicle.

In another embodiment, responsive to the request for the breath sample, determining a breath alcohol content (BrAC) of the breath sample as received at the portable breath alcohol monitoring device and determining the violation when the BrAC is above a predetermined BrAC threshold.

In yet another variation, a likely driving status of a user of the portable breath alcohol monitoring device can be ascertained based on capturing a plurality of successive images of the user within a vehicle in conjunction with the breath test request until the test is in the driver's seat of the vehicle, and driving the vehicle in violation of a prohibition against vehicle operation.

Contemporaneously with the request for providing of a breath sample, one or more camera images may be captured for identifying and authenticating a user of the portable breath alcohol monitoring device. It is also contemplated that other images captured can be used to at least partly determine a driving status of the user; for instance, use of wide angle camera devices in fixed locations within the vehicle to ascertain whether the user appears to be, or likely is, driving the vehicle. Capturing successive images in this manner pre-empts circumvention attempts, such as where a user can switch can out of a driver's seat position within the vehicle to avoid a violation.

In embodiments, authenticating the user of portable breath alcohol monitoring device 101 comprises comparing the captured image of the user with a predesignated image stored in memory 202 of portable breath alcohol monitoring device. In alternate embodiments, the predesignated image can be stored in a memory of violation report server 102, and the authenticating is performed at violation report server 102.

At step 340, reporting the violation to remote violation report server 102 communicatively coupled to portable breath alcohol monitoring device 101.

In some embodiments, the predetermined BAC threshold is stored in memory 202 of portable breath alcohol monitoring device 101. In alternate embodiments, the predetermined BAC threshold can stored in a memory of violation report server 102, and made communicatively accessible to portable breath alcohol monitoring device 101.

In some embodiments, the violation comprises an impaired driving violation, and reporting the violation comprises identifying the assigned user of portable breath alcohol monitoring device 101 in conjunction with at least the BrAC as determined, or a BAC correlated with the BrAC as measured. In alternate embodiments, all BrAC readings acquired at portable alcohol breath monitoring device 101 can be forwarded to server 102, without determination as to a violation. Instead, in such alternate embodiments, a violation can be determined in conjunction with violation report module 103 of server device 102 based on actual BrAC measurements as received from portable breath alcohol monitoring device 101.

In another variation, it is contemplated that some aspects of the method be performed at violation report server device 102, while other aspects that require sensing functions via sensor devices 205 be performed at portable alcohol breath monitoring device 101. In such aspects, user related data, including rate of motion data, breath sample data and digital images data acquired in conjunction with portable alcohol breath monitoring device 101 can be communicated in real time via communication interface 207 and network 104 to violation report server 102 to determine violation decisions there. In these embodiments, violation report server device 102 can include a processor and a non-transitory memory including instructions. The instructions when executed in the processor cause operations comprising inferring a rate of motion associated with portable breath alcohol monitoring device 101 communicatively coupled with the server computing device. Initiating, at display screen 203 of portable breath alcohol monitoring device 101 when the rate of motion is above a predetermined threshold, a request for a breath sample. Then determining, responsive to the request for the breath sample at the portable breath alcohol monitoring device 101, a violation.

It is contemplated for embodiments described herein to extend to individual elements and concepts described herein, independently of other concepts, ideas or system, as well as for embodiments to include combinations of elements recited anywhere in this application. For example, although techniques described herein are disclosed in context of alcohol sensor devices and alcohol impaired driving, it is contemplated that such techniques, in conjunction with appropriate, respective sensor devices, be applied to alternate intoxicant agents that result in impaired driving. Such intoxicants can include, but not necessarily be limited to, drugs including cannabinoids, opiates, and methamphetamines.

Although embodiments are described in detail herein with reference to the accompanying drawings, it is contemplated that the disclosure herein is not limited to only such literal embodiments. As such, many modifications including variations in sequence of the method steps in conjunction with varying combinations of user interface features disclosed herein will be apparent to practitioners skilled in this art. Accordingly, it is intended that the scope of the invention be defined by the following claims and their equivalents. Furthermore, it is contemplated that a particular feature described either individually or as part of an embodiment can be combined with other individually described features, or parts of other embodiments. Thus, the absence of describing combinations of such do not preclude the inventor from claiming rights to such combinations.

What is claimed is:

1. A method of deploying a portable breath alcohol monitoring device, the method comprising:
   inferring a rate of motion associated with the portable breath alcohol monitoring device;
   initiating, at a display screen of the portable breath alcohol monitoring device when the rate of motion is above a predetermined threshold, a request for a breath sample;
   authenticating a user of the portable breath alcohol monitoring device based on capturing a plurality of successive images of the user within a vehicle;
   ascertaining a likely driving status of the user based on the plurality of successive images at a monitoring logic module;
   determining a violation responsive to the request for the breath sample and responsive to ascertaining the likely driving status of the user as a driver of the vehicle; and
   reporting the violation to a remote server communicatively coupled to the portable breath alcohol monitoring device, wherein reporting the violation comprises identifying an assigned user of the portable breath alcohol monitoring device in conjunction with a timestamp and the rate of motion.

2. The method of claim 1 wherein the authenticating comprises comparing at least one image as captured of the plurality of successive images with a predesignated image stored in a memory of the portable breath alcohol monitoring device.

3. The method of claim 1 further comprising determining the violation upon not receiving the breath sample subsequent to the request at the portable breath alcohol monitoring device.

4. The method of claim 1 further comprising, responsive to the request for the breath sample, determining a breath alcohol content (BrAC) of the breath sample as received at the portable breath alcohol monitoring device and determining the violation when the BrAC is above a predetermined BrAC threshold.

5. The method of claim 1 further comprising determining at least two successive coordinate positions traversed by the portable breath alcohol monitoring device using data acquired from a global positioning system.

6. The method of claim 5 wherein the inferring comprises calculating the rate of motion of the portable breath alcohol monitoring device based at least on an elapsed time duration associated with traversal between the at least two successive coordinate positions.

7. The method of claim 1 further comprising, prior to the inferring, receiving an indication that the portable breath alcohol monitoring device is in motion based at least in part upon data acquired from an accelerometer sensor device.

8. The method of claim 1 wherein the capturing the plurality of successive images is performed by a wide-angle camera disposed in a fixed location within the vehicle.

9. The method of claim 1 wherein determining the violation is further responsive to input received or not received within a time period after the request for the breath sample.

10. The method of claim 1 wherein determining the violation is performed at the monitoring logic module of the portable breath alcohol monitoring device.

11. The method of claim 1 wherein ascertaining a likely driving status of the user is performed at the monitoring logic module of the portable breath alcohol monitoring device.

12. A computing device comprising:
    a processor; and
    a non-transitory memory including instructions, the instructions when executed in the processor causing operations comprising:
    inferring a rate of motion associated with a portable breath alcohol monitoring device;
    initiating, at a display screen of the portable breath alcohol monitoring device when the rate of motion is above a predetermined threshold, a request for a breath sample;
    authenticating a user of the portable breath alcohol monitoring device based on capturing a plurality of successive images of the user within a vehicle, wherein the capturing the plurality of successive images is performed by a wide-angle camera disposed in a fixed location within the vehicle;
    ascertaining a likely driving status of the user based on the plurality of successive images at a monitoring logic module;
    determining a violation responsive to the request for the breath sample and responsive to ascertaining the likely driving status of the user as a driver of the vehicle; and
    reporting the violation to a remote server communicatively coupled to the portable breath alcohol monitoring device.

13. The computing device of claim 12 wherein the authenticating comprises comparing at least one image as captured of the plurality of successive images with a predesignated image stored in a memory of the portable breath alcohol monitoring device.

14. The computing device of claim 12 further comprising instructions causing determining the violation upon not receiving the breath sample subsequent to the request at the portable breath alcohol monitoring device.

15. The computing device of claim 12 further comprising instructions causing, responsive to the request for the breath sample, determining a breath alcohol content (BrAC) of the breath sample as received at the portable breath alcohol monitoring device and determining the violation when the BrAC is above a predetermined BrAC threshold.

16. The computing device of claim 12 further comprising instructions causing determining at least two successive coordinate positions traversed by the portable breath alcohol monitoring device using data acquired from a global positioning system.

17. The computing device of claim 16 wherein the inferring comprises calculating the rate of motion of the portable breath alcohol monitoring device based at least on an elapsed time duration associated with traversal between the at least two successive coordinate positions.

18. The computing device of claim 12 wherein reporting the violation comprises identifying an assigned user of the portable breath alcohol monitoring device in conjunction with a timestamp and the rate of motion.

19. A portable breath alcohol monitoring device comprising:
- a processor; and
- a memory including instructions, the instructions when executed in the processor causing operations comprising:
- inferring a rate of motion associated with the portable breath alcohol monitoring device;
- initiating, at a display screen of the portable breath alcohol monitoring device when the rate of motion is above a predetermined threshold, a request for a breath sample;
- authenticating a user of the portable breath alcohol monitoring device based on capturing a plurality of successive images of the user within a vehicle;
- ascertaining a likely driving status of the user based on the plurality of successive images at a monitoring logic module;
- determining a violation at the monitoring logic module of the portable breath alcohol monitoring device responsive to the request for the breath sample and responsive to ascertaining the likely driving status of the user as a driver of the vehicle; and
- reporting the violation to a remote server communicatively coupled to the portable breath alcohol monitoring device, wherein reporting the violation comprises identifying an assigned user of the portable breath alcohol monitoring device in conjunction with a timestamp and the rate of motion.

* * * * *